US008199187B2

(12) United States Patent
Knapp, II et al.

(10) Patent No.: US 8,199,187 B2

(45) Date of Patent: Jun. 12, 2012

(54) ADAPTER FOR USE WITH DIGITAL IMAGING MEDICAL DEVICE

(75) Inventors: Keith N. Knapp, II, Townsend, MA (US); Daniel Braunstein, Arlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1839 days.

(21) Appl. No.: 11/241,881

(22) Filed: Sep. 30, 2005

(65) Prior Publication Data

US 2006/0114986 A1 Jun. 1, 2006

Related U.S. Application Data

(60) Provisional application No. 60/614,879, filed on Sep. 30, 2004.

(51) Int. Cl.

*A62B 1/04* (2006.01)
*H04N 5/76* (2006.01)
*H04N 5/222* (2006.01)

(52) U.S. Cl. .................. 348/65; 348/333.02; 348/231.3; 348/231.6

(58) Field of Classification Search .................... 348/65, 348/333.02, 231.3, 231.6
See application file for complete search history.

(56) References Cited

U.S. PATENT DOCUMENTS 3,266,059 A 8/1966 Stelle
3,470,876 A 10/1969 Barchilon
3,572,325 A 3/1971 Bazell et al.
3,581,738 A 6/1971 Moore
4,108,211 A 8/1978 Tanaka
4,286,585 A 9/1981 Ogawa
4,294,162 A 10/1981 Fowler et al.
4,311,134 A 1/1982 Mitsui et al.
4,315,309 A 2/1982 Coli
4,351,323 A 9/1982 Ouchi et al.
4,425,113 A 1/1984 Bilstad
4,432,349 A 2/1984 Oshiro
4,471,766 A 9/1984 Terayama
4,473,841 A 9/1984 Murakoshi et al.
4,488,039 A 12/1984 Sato et al.
4,491,865 A 1/1985 Danna et al.
4,493,537 A 1/1985 Nakahashi
4,495,134 A 1/1985 Ouchi et al.
4,499,895 A 2/1985 Takayama
4,503,842 A 3/1985 Takayama
4,513,235 A 4/1985 Acklam et al.
4,515,444 A 5/1985 Prescott et al.
4,516,063 A 5/1985 Kaye et al.
4,519,391 A 5/1985 Murakoshi
4,552,130 A 11/1985 Kinoshita
(Continued)

FOREIGN PATENT DOCUMENTS

EP 0 075 153 B1 6/1987
(Continued)

*Primary Examiner* — Houshang Safaipour

(74) *Attorney, Agent, or Firm* — Finnegan, Henderson, Farabow, Garrett & Dunner, LLP

(57) ABSTRACT

An adapter that allows digital imaging devices to be used with existing analog consoles. In one embodiment of the invention, an adaptor is provided that receives a digital video image signal from a medical device and converts the digital signal into an analog signal that can be displayed by an analog console. In another embodiment, the invention provides a method for converting a digital video signal received from a medical imaging device into a standardized analog video format.

18 Claims, 7 Drawing Sheets

300 310 312 313 302 320 303 304 LED CLOCK RECEIVER CMOS IMAGER THERMISTOR POWER REGULATOR LED 305 308 316 330 CLOCK SIGNAL (356) DIGITAL VIDEO (314) I²C INTERFACE (358) SENSOR SIGNAL (374) IMAGER POWER (388) LED POWER #1 (384) LED POWER #2 (386) 500 352 354 394 350 MOTHERBOARD CPU AND MASTER CLOCK CAMERA CARD WITH DESERIALIZER SENSOR RECEIVER POWER GROUND 360 372 380 382 IMAGE PROCESSOR D/A CONVERTOR AND ANALOG ENCODER MEMORY NETWORK INTERFACE 364 366 390 392 DIGITAL VIDEO OUTPUT ANALOG VIDEO OUTPUT NETWORK CONNECTION

U.S. PATENT DOCUMENTS

| | | | |
|---|---|---|---|
| 4,559,928 A | 12/1985 | Takayama | |
| 4,566,437 A | 1/1986 | Yamaguchi | |
| 4,573,450 A | 3/1986 | Arakawa | |
| 4,580,210 A | 4/1986 | Nordstrom | |
| 4,586,923 A | 5/1986 | Gould et al. | |
| 4,615,330 A | 10/1986 | Nagasaki et al. | |
| 4,616,630 A | 10/1986 | Arakawa | |
| 4,617,915 A | 10/1986 | Arakawa | |
| 4,618,884 A | 10/1986 | Nagasaki | |
| 4,621,618 A | 11/1986 | Omagari et al. | |
| 4,622,584 A | 11/1986 | Nagasaki et al. | |
| 4,625,714 A | 12/1986 | Toyota | |
| 4,631,582 A | 12/1986 | Nagasaki et al. | |
| 4,633,303 A | 12/1986 | Nagasaki et al. | |
| 4,633,304 A | 12/1986 | Nagasaki | |
| 4,643,170 A | 2/1987 | Miyazaki et al. | |
| 4,646,723 A | 3/1987 | Arakawa | |
| 4,649,904 A | 3/1987 | Krauter et al. | |
| 4,651,202 A | 3/1987 | Arakawa | |
| 4,652,093 A | 3/1987 | Stephen et al. | |
| 4,652,916 A | 3/1987 | Suzaki et al. | |
| 4,654,701 A | 3/1987 | Yabe | |
| RE32,421 E | 5/1987 | Hattori | |
| 4,662,725 A | 5/1987 | Nisioka | |
| 4,663,657 A | 5/1987 | Nagasaki et al. | |
| 4,667,655 A | 5/1987 | Ogiu et al. | |
| 4,674,844 A | 6/1987 | Nishioka et al. | |
| 4,686,963 A | 8/1987 | Cohen et al. | |
| 4,697,210 A | 9/1987 | Toyota et al. | |
| 4,700,693 A | 10/1987 | Lia et al. | |
| 4,714,075 A | 12/1987 | Krauter et al. | |
| 4,716,457 A | 12/1987 | Matsuo | |
| 4,719,508 A | 1/1988 | Sasaki et al. | |
| 4,727,417 A | 2/1988 | Kanno et al. | |
| 4,727,418 A | 2/1988 | Kato et al. | |
| 4,745,470 A | 5/1988 | Yabe et al. | |
| 4,745,471 A | 5/1988 | Takamura et al. | |
| 4,746,974 A | 5/1988 | Matsuo | |
| 4,748,970 A | 6/1988 | Nakajima | |
| 4,755,029 A | 7/1988 | Okobe | |
| 4,762,119 A | 8/1988 | Allred et al. | |
| 4,765,312 A | 8/1988 | Sasa et al. | |
| 4,766,489 A | 8/1988 | Kato | |
| 4,787,369 A | 11/1988 | Allred et al. | |
| 4,790,294 A | 12/1988 | Allred et al. | |
| 4,794,913 A | 1/1989 | Shimonaka et al. | |
| 4,796,607 A | 1/1989 | Allred et al. | |
| 4,800,869 A | 1/1989 | Nakajima | |
| 4,805,596 A | 2/1989 | Hatori | |
| 4,806,011 A | 2/1989 | Bettinger | |
| 4,819,065 A | 4/1989 | Eino | |
| 4,819,077 A | 4/1989 | Kikuchi et al. | |
| 4,821,116 A | 4/1989 | Nagasaki et al. | |
| 4,824,225 A | 4/1989 | Nishioka | |
| 4,831,437 A | 5/1989 | Nishioka et al. | |
| 4,836,187 A | 6/1989 | Iwakoshi et al. | |
| 4,844,052 A | 7/1989 | Iwakoshi et al. | |
| 4,844,071 A | 7/1989 | Chen et al. | |
| 4,845,553 A | 7/1989 | Konomura et al. | |
| 4,845,555 A | 7/1989 | Yabe et al. | |
| 4,847,694 A | 7/1989 | Nishihara | |
| 4,853,772 A | 8/1989 | Kikuchi | |
| 4,860,731 A | 8/1989 | Matsuura | |
| 4,867,546 A | 9/1989 | Nishioka et al. | |
| 4,868,647 A | 9/1989 | Uehara et al. | |
| 4,869,237 A | 9/1989 | Eino et al. | |
| 4,869,256 A * | 9/1989 | Kanno et al. | 600/440 |
| 4,873,965 A | 10/1989 | Danieli | |
| 4,875,468 A | 10/1989 | Krauter et al. | |
| 4,877,314 A | 10/1989 | Kanamori | |
| 4,882,623 A | 11/1989 | Uchikubo | |
| 4,884,134 A | 11/1989 | Tsuji et al. | |
| 4,885,634 A | 12/1989 | Yabe | |
| 4,890,159 A | 12/1989 | Ogiu | |
| 4,894,715 A | 1/1990 | Uchikubo et al. | |
| 4,895,431 A | 1/1990 | Tsujiuchi et al. | |
| 4,897,789 A | 1/1990 | King et al. | |
| 4,899,731 A | 2/1990 | Takayama et al. | |
| 4,899,732 A | 2/1990 | Cohen | |
| 4,899,787 A | 2/1990 | Ouchi et al. | |
| 4,905,666 A | 3/1990 | Fukuda | |
| 4,918,521 A | 4/1990 | Yabe et al. | |
| 4,919,112 A | 4/1990 | Siegmund | |
| 4,919,114 A | 4/1990 | Miyazaki | |
| 4,920,980 A | 5/1990 | Jackowski | |
| 4,928,172 A | 5/1990 | Uehara et al. | |
| 4,931,867 A | 6/1990 | Kikuchi | |
| 4,941,454 A | 7/1990 | Wood et al. | |
| 4,941,456 A | 7/1990 | Wood et al. | |
| 4,951,134 A | 8/1990 | Nakasima et al. | |
| 4,951,135 A | 8/1990 | Sasagawa et al. | |
| 4,952,040 A | 8/1990 | Igarashi | |
| 4,960,127 A | 10/1990 | Noce et al. | |
| 4,961,110 A | 10/1990 | Nakamura | |
| 4,967,269 A | 10/1990 | Sasagawa et al. | |
| 4,971,034 A | 11/1990 | Doi et al. | |
| 4,973,311 A | 11/1990 | Iwakoshi et al. | |
| 4,979,497 A | 12/1990 | Matsuura et al. | |
| 4,982,725 A | 1/1991 | Hibino et al. | |
| 4,984,878 A | 1/1991 | Miyano | |
| 4,986,642 A | 1/1991 | Yokota et al. | |
| 4,987,884 A | 1/1991 | Nishioka et al. | |
| 4,989,075 A | 1/1991 | Ito | |
| 4,989,581 A | 2/1991 | Tamburrino et al. | |
| 4,996,974 A | 3/1991 | Ciarlei | |
| 4,996,975 A | 3/1991 | Nakamura | |
| 5,001,556 A | 3/1991 | Nakamura et al. | |
| 5,005,558 A | 4/1991 | Aomori | |
| 5,005,957 A | 4/1991 | Kanamori et al. | |
| 5,007,408 A | 4/1991 | Ieoka | |
| 5,018,509 A | 5/1991 | Suzuki et al. | |
| 5,022,382 A | 6/1991 | Ohshoki et al. | |
| 5,029,016 A | 7/1991 | Hiyama et al. | |
| 5,034,888 A | 7/1991 | Uehara et al. | |
| 5,040,069 A | 8/1991 | Matsumoto et al. | |
| RE33,689 E | 9/1991 | Nishioka et al. | |
| 5,045,935 A | 9/1991 | Kikuchi | |
| 5,049,989 A | 9/1991 | Tsuji | |
| 5,050,584 A | 9/1991 | Matsuura | |
| 5,050,974 A | 9/1991 | Takasugi et al. | |
| 5,056,503 A | 10/1991 | Nagasaki | |
| 5,061,994 A | 10/1991 | Takahashi | |
| 5,068,719 A | 11/1991 | Tsuji | |
| 5,074,861 A | 12/1991 | Schneider et al. | |
| 5,081,524 A | 1/1992 | Tsuruoka et al. | |
| 5,087,989 A | 2/1992 | Igarashi | |
| 5,110,645 A | 5/1992 | Matsumoto et al. | |
| 5,111,281 A | 5/1992 | Sekiguchi | |
| 5,111,306 A | 5/1992 | Kanno et al. | |
| 5,111,804 A | 5/1992 | Funakoshi | |
| 5,113,254 A | 5/1992 | Kanno et al. | |
| 5,119,238 A | 6/1992 | Igarashi | |
| 5,131,393 A | 7/1992 | Ishiguro et al. | |
| 5,137,013 A | 8/1992 | Chiba et al. | |
| 5,140,265 A | 8/1992 | Sakiyama et al. | |
| 5,159,446 A | 10/1992 | Hibino et al. | |
| 5,170,775 A | 12/1992 | Tagami | |
| 5,172,225 A | 12/1992 | Takahashi et al. | |
| 5,174,293 A | 12/1992 | Hagiwara | |
| 5,176,629 A | 1/1993 | Kullas et al. | |
| 5,191,878 A | 3/1993 | Iida et al. | |
| 5,198,931 A | 3/1993 | Igarashi | |
| 5,201,908 A | 4/1993 | Jones | |
| 5,208,702 A | 5/1993 | Shiraiwa | |
| 5,209,220 A | 5/1993 | Hiyama et al. | |
| 5,225,958 A | 7/1993 | Nakamura | |
| 5,228,356 A | 7/1993 | Chuang | |
| 5,243,416 A | 9/1993 | Nakazawa | |
| 5,243,967 A | 9/1993 | Hibino | |
| 5,257,628 A | 11/1993 | Ishiguro et al. | |
| 5,271,381 A | 12/1993 | Ailinger et al. | |
| RE34,504 E | 1/1994 | Uehara et al. | |
| 5,291,010 A | 3/1994 | Tsuji | |
| 5,299,559 A | 4/1994 | Bruce et al. | |
| 5,311,858 A | 5/1994 | Adair | |
| 5,325,845 A | 7/1994 | Adair et al. | |
| 5,331,551 A | 7/1994 | Tsuruoka et al. | |

5,342,299 A 8/1994 Snoke et al.
5,347,989 A 9/1994 Monroe et al.
5,374,953 A 12/1994 Sasaki et al.
5,379,757 A 1/1995 Hiyama et al.
5,381,782 A 1/1995 DeLaRama et al.
5,390,662 A 2/1995 Okada
5,400,769 A 3/1995 Tanii et al.
5,402,768 A 4/1995 Adair
5,402,769 A 4/1995 Tsuji
5,409,485 A 4/1995 Suda
5,412,478 A 5/1995 Ishihara et al.
5,418,649 A 5/1995 Igarashi
5,420,644 A 5/1995 Watanabe
5,431,645 A 7/1995 Smith et al.
5,434,615 A 7/1995 Matumoto
5,436,640 A 7/1995 Reeves
5,436,767 A 7/1995 Suzuki et al.
5,440,341 A 8/1995 Suzuki et al.
5,464,007 A 11/1995 Krauter et al.
5,469,840 A 11/1995 Tanii et al.
5,473,235 A 12/1995 Lance et al.
5,482,029 A 1/1996 Sekiguchi et al.
5,484,407 A 1/1996 Osypka
5,485,316 A 1/1996 Mori et al.
5,496,260 A 3/1996 Krauter et al.
5,515,449 A 5/1996 Tsuruoka et al.
5,518,501 A 5/1996 Oneda et al.
5,518,502 A 5/1996 Kaplan et al.
5,543,831 A 8/1996 Tsuji et al.
5,569,158 A 10/1996 Suzuki et al.
5,569,159 A 10/1996 Anderson et al.
5,586,262 A 12/1996 Komatsu et al.
5,589,854 A 12/1996 Tsai
5,591,202 A 1/1997 Slater et al.
5,608,451 A 3/1997 Konno et al.
5,619,380 A 4/1997 Agasawa et al.
5,622,528 A 4/1997 Hamano et al.
5,631,695 A 5/1997 Nakamura et al.
5,633,203 A 5/1997 Adair
5,643,203 A 7/1997 Beiser et al.
5,645,075 A 7/1997 Palmer et al.
5,647,840 A 7/1997 D'Amelio et al.
5,658,238 A 8/1997 Suzuki et al.
5,667,477 A 9/1997 Segawa
5,674,182 A 10/1997 Suzuki et al.
5,674,197 A 10/1997 van Muiden et al.
5,685,823 A 11/1997 Ito et al.
5,685,825 A 11/1997 Takase et al.
5,691,853 A 11/1997 Miyano
5,695,450 A 12/1997 Yabe et al.
5,698,866 A 12/1997 Doiron et al.
5,702,349 A 12/1997 Morizumi
5,702,754 A 12/1997 Zhong
5,703,724 A 12/1997 Miyano
5,704,371 A 1/1998 Shepard
5,704,896 A 1/1998 Fukunishi et al.
5,708,482 A 1/1998 Takahashi et al.
5,721,566 A 2/1998 Rosenberg et al.
5,724,068 A 3/1998 Sanchez et al.
5,728,045 A 3/1998 Komi
5,739,811 A 4/1998 Rosenberg et al.
5,740,801 A 4/1998 Branson
5,746,696 A 5/1998 Kondo
5,755,760 A 5/1998 Maguire et al.
5,764,809 A 6/1998 Nomami et al.
5,767,839 A 6/1998 Rosenberg
5,779,686 A 7/1998 Sato et al.
5,781,172 A 7/1998 Engel et al.
5,788,714 A 8/1998 Ouchi
5,789,047 A 8/1998 Sasaki et al.
5,793,539 A 8/1998 Konno et al.
5,805,140 A 9/1998 Rosenberg et al.
5,810,715 A 9/1998 Moriyama
5,812,983 A 9/1998 Kumagai
5,819,736 A 10/1998 Avny et al.
5,820,591 A 10/1998 Thompson et al.
5,821,466 A 10/1998 Clark et al.
5,821,920 A 10/1998 Rosenberg et al.
5,823,948 A 10/1998 Ross, Jr. et al.
5,827,186 A 10/1998 Chen et al.
5,827,190 A 10/1998 Palcic et al.
5,828,197 A 10/1998 Martin et al.
5,828,363 A 10/1998 Yaniger et al.
5,830,124 A 11/1998 Suzuki et al.
5,830,128 A 11/1998 Tanaka
5,836,869 A 11/1998 Kudo et al.
5,837,023 A 11/1998 Koike et al.
5,840,014 A 11/1998 Miyano et al.
5,841,126 A 11/1998 Fossum et al.
5,843,000 A 12/1998 Nishioka et al.
5,846,183 A 12/1998 Chilcoat
5,855,560 A 1/1999 Idaomi et al.
5,857,963 A 1/1999 Pelchy et al.
5,865,724 A 2/1999 Palmer et al.
5,868,664 A 2/1999 Speier et al.
5,868,666 A 2/1999 Okada et al.
5,873,816 A 2/1999 Kagawa et al.
5,873,866 A 2/1999 Kondo et al.
5,876,326 A 3/1999 Takamura et al.
5,876,331 A 3/1999 Wu et al.
5,876,373 A 3/1999 Giba et al.
5,876,427 A 3/1999 Chen et al.
5,877,819 A 3/1999 Branson
5,879,284 A 3/1999 Tsujita
5,880,714 A 3/1999 Rosenberg et al.
5,882,293 A 3/1999 Ouchi
5,882,339 A 3/1999 Beiser et al.
5,889,670 A 3/1999 Schuler et al.
5,889,672 A 3/1999 Schuler et al.
5,892,630 A 4/1999 Broome
5,895,350 A 4/1999 Hori
5,897,507 A 4/1999 Kortenbach et al.
5,897,525 A 4/1999 Dey et al.
5,907,487 A 5/1999 Rosenberg et al.
5,923,018 A 7/1999 Kameda et al.
5,928,136 A 7/1999 Barry
5,929,607 A 7/1999 Rosenberg et al.
5,929,846 A 7/1999 Rosenberg et al.
5,929,900 A 7/1999 Yamanaka
5,929,901 A 7/1999 Adair et al.
5,931,833 A 8/1999 Silverstein
5,933,809 A 8/1999 Hunt et al.
5,935,085 A 8/1999 Welsh et al.
5,936,778 A 8/1999 Miyano et al.
5,941,817 A 8/1999 Crawford
5,950,168 A 9/1999 Simborg et al.
5,951,462 A 9/1999 Yamanaka
5,956,416 A 9/1999 Tsuruoka et al.
5,956,689 A 9/1999 Everhart
5,956,690 A 9/1999 Haggerson et al.
5,959,613 A 9/1999 Rosenberg et al.
5,963,270 A * 10/1999 Hwang ........................ 348/588
5,976,070 A 11/1999 Ono et al.
5,976,074 A 11/1999 Moriyama
5,980,454 A 11/1999 Broome
5,980,468 A 11/1999 Zimmon
5,986,693 A 11/1999 Adair et al.
5,991,729 A 11/1999 Barry et al.
5,991,730 A 11/1999 Lubin et al.
5,999,168 A 12/1999 Rosenberg et al.
6,002,425 A 12/1999 Yamanaka et al.
6,007,482 A 12/1999 Madni et al.
6,007,531 A 12/1999 Snoke et al.
6,014,630 A 1/2000 Jeacock et al.
6,015,088 A 1/2000 Parker et al.
6,017,322 A 1/2000 Snoke et al.
6,020,875 A 2/2000 Moore et al.
6,020,876 A 2/2000 Rosenberg et al.
6,026,363 A 2/2000 Shepard
6,030,360 A 2/2000 Biggs
6,032,120 A 2/2000 Rock et al.
6,039,728 A 3/2000 Berlien et al.
6,043,839 A 3/2000 Adair et al.
6,050,718 A 4/2000 Schena et al.
6,057,828 A 5/2000 Schena et al.
6,059,719 A 5/2000 Yamamoto et al.
6,061,004 A 5/2000 Rosenberg
6,067,077 A 5/2000 Martin et al.

6,071,248 A 6/2000 Zimmon
6,075,555 A 6/2000 Street
6,078,308 A 6/2000 Rosenberg et al.
6,078,353 A 6/2000 Yamanaka et al.
6,078,876 A 6/2000 Rosenberg et al.
6,080,104 A 6/2000 Ozawa et al.
6,081,809 A 6/2000 Kumagai
6,083,152 A 7/2000 Strong
6,083,170 A 7/2000 Ben-Haim
6,095,971 A 8/2000 Takahashi
6,099,465 A 8/2000 Inoue
6,100,874 A 8/2000 Schena et al.
6,104,382 A 8/2000 Martin et al.
6,120,435 A 9/2000 Eino
6,125,337 A 9/2000 Rosenberg et al.
6,128,006 A 10/2000 Rosenberg et al.
6,132,369 A 10/2000 Takahashi
6,134,056 A 10/2000 Nakamura
6,134,506 A 10/2000 Rosenberg et al.
6,135,946 A 10/2000 Konen et al.
6,139,508 A 10/2000 Simpson et al.
6,141,037 A 10/2000 Upton et al.
6,142,956 A 11/2000 Kortenbach et al.
6,146,355 A 11/2000 Biggs
6,149,607 A 11/2000 Simpson et al.
6,152,877 A 11/2000 Masters
6,154,198 A 11/2000 Rosenberg
6,154,248 A 11/2000 Ozawa et al.
6,154,870 A 11/2000 Fredrickson et al.
6,155,988 A 12/2000 Peters
6,181,481 B1 1/2001 Yamamoto et al.
6,184,922 B1 2/2001 Saito et al.
6,193,714 B1 2/2001 McGaffigan et al.
6,195,592 B1 2/2001 Schuler et al.
6,203,493 B1 3/2001 Ben-Haim
6,206,824 B1 3/2001 Ohara et al.
6,211,904 B1 4/2001 Adair
6,216,104 B1 4/2001 Moshfeghi et al.
6,219,091 B1 4/2001 Yamanaka et al.
6,221,070 B1 4/2001 Tu et al.
6,238,799 B1 5/2001 Opolski
6,241,668 B1 6/2001 Herzog
6,260,994 B1 7/2001 Matsumoto et al.
6,272,470 B1 8/2001 Teshima
6,275,255 B1 8/2001 Adair et al.
6,283,960 B1 9/2001 Ashley
6,295,082 B1 9/2001 Dowdy et al.
6,299,625 B1 10/2001 Bacher
6,309,347 B1 10/2001 Takahashi et al.
6,310,642 B1 10/2001 Adair et al.
6,319,196 B1 11/2001 Minami
6,319,197 B1 11/2001 Tsuji et al.
6,334,844 B1 1/2002 Akiba
6,346,075 B1 2/2002 Arai et al.
6,366,799 B1 4/2002 Acker et al.
6,381,029 B1 4/2002 Tipirneni
6,398,724 B1 6/2002 May et al.
6,413,207 B1 7/2002 Minami
6,421,078 B1 7/2002 Akai et al.
6,425,535 B1 7/2002 Akiba
6,425,858 B1 7/2002 Minami
6,436,032 B1 8/2002 Eto et al.
6,441,845 B1 8/2002 Matsumoto
6,447,444 B1 9/2002 Avni et al.
6,449,006 B1 9/2002 Shipp
6,453,190 B1 9/2002 Acker et al.
6,454,162 B1 9/2002 Teller
6,459,447 B1 10/2002 Okada et al.
6,468,204 B2 10/2002 Sendai et al.
6,475,141 B2 11/2002 Abe
6,478,730 B1 11/2002 Bala et al.
6,489,987 B1 12/2002 Higuchi et al.
6,496,827 B2 12/2002 Kozam et al.
6,498,948 B1 12/2002 Ozawa et al.
6,503,193 B1 1/2003 Iwasaki et al.
6,520,908 B1 2/2003 Ikeda et al.
6,524,234 B2 2/2003 Ouchi
6,530,882 B1 3/2003 Farkas et al.
6,533,722 B2 3/2003 Nakashima
6,540,669 B2 4/2003 Abe et al.
6,544,194 B1 4/2003 Kortenbach et al.
6,545,703 B1 4/2003 Takahashi et al.
6,551,239 B2 4/2003 Renner et al.
6,558,317 B2 5/2003 Takahashi et al.
6,561,971 B1 5/2003 Akiba
6,565,507 B2 5/2003 Kamata et al.
6,574,629 B1 6/2003 Cooke, Jr. et al.
6,589,162 B2 7/2003 Nakashima et al.
6,595,913 B2 7/2003 Takahashi
6,597,390 B1 7/2003 Higuchi
6,599,239 B2 7/2003 Hayakawa et al.
6,602,186 B1 8/2003 Sugimoto et al.
6,605,035 B2 8/2003 Ando et al.
6,609,135 B1 8/2003 Omori et al.
6,611,846 B1 8/2003 Stoodley
6,614,969 B2 9/2003 Eichelberger et al.
6,616,601 B2 9/2003 Hayakawa
6,623,424 B2 9/2003 Hayakawa et al.
6,638,214 B2 10/2003 Akiba
6,638,215 B2 10/2003 Kobayashi
6,641,528 B2 11/2003 Torii
6,651,669 B1 11/2003 Burnside
6,656,110 B1 12/2003 Irion et al.
6,656,112 B2 12/2003 Miyanaga
6,659,940 B2 12/2003 Adler
6,663,561 B2 12/2003 Sugimoto et al.
6,669,629 B2 12/2003 Matsui
6,673,012 B2 1/2004 Fujii et al.
6,677,984 B2 1/2004 Kobayashi et al.
6,678,397 B1 1/2004 Omori et al.
6,682,479 B1 1/2004 Takahashi et al.
6,685,631 B2 2/2004 Minami
6,686,949 B2 2/2004 Kobayashi et al.
6,690,409 B1 2/2004 Takahashi
6,690,963 B2 2/2004 Ben-Haim et al.
6,692,431 B2 2/2004 Kazakevich
6,697,101 B1 2/2004 Takahashi et al.
6,699,181 B2 3/2004 Wako
6,702,737 B2 3/2004 Hinto et al.
6,711,426 B2 3/2004 Benaron et al.
6,715,068 B1 3/2004 Kazunori
6,716,162 B2 4/2004 Hakamata
6,728,599 B2 4/2004 Wang et al.
6,730,018 B2 5/2004 Takase
6,736,773 B2 5/2004 Wendlandt et al.
6,743,240 B2 6/2004 Smith et al.
6,749,559 B1 6/2004 Kraas et al.
6,749,560 B1 6/2004 Konstorum et al.
6,749,561 B2 6/2004 Kazakevich
6,753,905 B1 6/2004 Okada et al.
6,758,806 B2 7/2004 Kamrava et al.
6,758,807 B2 7/2004 Minami
6,758,842 B2 7/2004 Irion et al.
6,778,208 B2 8/2004 Takeshige et al.
6,780,151 B2 8/2004 Grabover et al.
6,785,410 B2 8/2004 Vining et al.
6,785,414 B1 8/2004 McStravick et al.
6,785,593 B2 8/2004 Wang et al.
6,796,938 B2 9/2004 Sendai
6,796,939 B1 9/2004 Hirata et al.
6,798,533 B2 9/2004 Tipirneni
6,800,056 B2 10/2004 Tartaglia et al.
6,800,057 B2 10/2004 Tsujita et al.
6,808,491 B2 10/2004 Kortenbach et al.
6,824,539 B2 11/2004 Novak
6,824,548 B2 11/2004 Smith et al.
6,829,003 B2 12/2004 Takami
6,830,545 B2 12/2004 Bendall
6,832,990 B2 12/2004 Kortenbach et al.
6,840,932 B2 1/2005 Lang et al.
6,842,196 B1 1/2005 Swift et al.
6,846,286 B2 1/2005 Suzuki et al.
6,847,933 B1 1/2005 Hastings
6,849,043 B2 2/2005 Kondo
6,850,794 B2 2/2005 Shahidi
6,855,109 B2 2/2005 Obata et al.
6,858,004 B1 2/2005 Ozawa et al.
6,858,014 B2 2/2005 Damarati 6,860,849 B2 3/2005 Matsushita et al.
6,863,650 B1 3/2005 Irion
6,863,661 B2 3/2005 Carrillo et al.
6,868,195 B2 3/2005 Fujita
6,871,086 B2 3/2005 Nevo et al.
6,873,352 B2 3/2005 Mochida et al.
6,876,380 B2 4/2005 Abe et al.
6,879,339 B2 4/2005 Ozawa
6,881,188 B2 4/2005 Furuya et al.
6,882,785 B2 4/2005 Eichelberger et al.
6,887,195 B1 5/2005 Pilvisto
6,890,294 B2 5/2005 Niwa et al.
6,892,090 B2 5/2005 Verard et al.
6,892,112 B2 5/2005 Wang et al.
6,895,268 B1 5/2005 Rahn et al.
6,898,086 B2 5/2005 Takami et al.
6,899,673 B2 5/2005 Ogura et al.
6,899,674 B2 5/2005 Viebach et al.
6,899,705 B2 5/2005 Niemeyer
6,900,777 B1 * 5/2005 Hebert et al. .................... 345/7
6,900,829 B1 5/2005 Ozawa et al.
6,902,527 B1 6/2005 Doguchi et al.
6,902,529 B2 6/2005 Onishi et al.
6,903,761 B1 6/2005 Abe et al.
6,903,883 B2 6/2005 Amanai
6,905,057 B2 6/2005 Swayze et al.
6,905,462 B1 6/2005 Homma
6,908,427 B2 6/2005 Fleener et al.
6,908,429 B2 6/2005 Heimberger et al.
6,911,916 B1 6/2005 Wang et al.
6,916,286 B2 7/2005 Kazakevich
6,923,818 B2 8/2005 Muramatsu et al.
6,928,490 B1 8/2005 Bucholz et al.
6,930,706 B2 8/2005 Kobayashi et al.
6,932,761 B2 8/2005 Maeda et al.
6,934,093 B2 8/2005 Kislev et al.
6,934,575 B2 8/2005 Ferre et al.
6,943,663 B2 9/2005 Wang et al.
6,943,821 B2 9/2005 Abe et al.
6,943,822 B2 9/2005 Iida et al.
6,943,946 B2 9/2005 Fiete
6,943,959 B2 9/2005 Homma
6,943,966 B2 9/2005 Konno
6,944,031 B2 9/2005 Takami et al.
6,949,068 B2 9/2005 Taniguchi et al.
6,950,248 B2 9/2005 Rudischhauser et al.
6,950,691 B2 9/2005 Uchikubo
6,954,311 B2 10/2005 Amanai
6,955,671 B2 10/2005 Uchikubo
6,956,703 B2 10/2005 Saito
6,961,187 B2 11/2005 Amanai
6,962,564 B2 11/2005 Hickle
6,963,175 B2 11/2005 Archenhold et al.
6,964,662 B2 11/2005 Kidooka et al.
6,967,673 B2 11/2005 Ozawa et al.
6,974,466 B2 12/2005 Ahmed et al.
6,975,968 B2 12/2005 Nakamitsu et al.
6,976,954 B2 12/2005 Takahashi
6,977,053 B2 12/2005 Mukasa et al.
6,977,670 B2 12/2005 Takahashi et al.
6,980,227 B2 12/2005 Iida et al.
6,980,921 B2 12/2005 Anderson et al.
6,981,945 B1 1/2006 Sarvazyan et al.
6,982,740 B2 1/2006 Adair et al.
6,984,206 B2 1/2006 Kumei et al.
6,985,183 B2 1/2006 Jan et al.
6,986,686 B2 1/2006 Shibata et al.
6,994,668 B2 2/2006 Miyano
6,994,704 B2 2/2006 Qin et al.
7,001,330 B2 2/2006 Kobayashi
7,008,376 B2 3/2006 Ikeda et al.
7,033,316 B2 * 4/2006 Takahashi .................... 600/118
7,504,230 B2 * 3/2009 Kauvar .......................... 435/7.6
7,623,176 B2 * 11/2009 Hoshino et al. .......... 348/333.02
2001/0039370 A1 11/2001 Takahashi et al.
2001/0049491 A1 12/2001 Shimada
2001/0050712 A1 * 12/2001 Dunton et al. ................ 348/220
2002/0017515 A1 2/2002 Obata et al.
2002/0028984 A1 3/2002 Hayakawa et al.
2002/0045801 A1 * 4/2002 Niida et al. .................. 600/118
2002/0055669 A1 5/2002 Konno
2002/0080248 A1 6/2002 Adair et al.
2002/0087048 A1 7/2002 Brock et al.
2002/0087166 A1 7/2002 Brock et al.
2002/0095175 A1 7/2002 Brock et al.
2002/0128633 A1 9/2002 Brock et al.
2002/0145661 A1 10/2002 Takahashi et al.
2002/0193662 A1 12/2002 Belson
2002/0193664 A1 12/2002 Ross et al.
2003/0034863 A1 2/2003 Kazakevich
2003/0065250 A1 4/2003 Chiel et al.
2003/0069897 A1 4/2003 Roy et al.
2003/0122927 A1 7/2003 Saito et al.
2003/0149338 A1 8/2003 Francois et al.
2003/0181905 A1 9/2003 Long
2004/0049097 A1 3/2004 Miyake
2004/0054258 A1 3/2004 Maeda et al.
2004/0073083 A1 4/2004 Ikeda et al.
2004/0073084 A1 4/2004 Meada et al.
2004/0073085 A1 4/2004 Ikeda et al.
2004/0143159 A1 7/2004 Wendlandt
2004/0147809 A1 7/2004 Kazakevich
2004/0167379 A1 8/2004 Akiba
2004/0249247 A1 12/2004 Iddan
2004/0257608 A1 12/2004 Tipirneni
2005/0094734 A1 * 5/2005 Parthasarathy ............... 375/257
2005/0192476 A1 9/2005 Homan et al.
2005/0197861 A1 9/2005 Omori et al.
2005/0200698 A1 9/2005 Amling et al.
2005/0203341 A1 9/2005 Welker et al.
2005/0203418 A1 9/2005 Yamada et al.
2005/0205958 A1 9/2005 Taniguchi et al.
2005/0207645 A1 9/2005 Nishimura et al.
2005/0209509 A1 9/2005 Belson
2005/0225872 A1 10/2005 Uzawa et al.
2005/0226508 A1 10/2005 Gotohda
2005/0228221 A1 10/2005 Hirakawa
2005/0228222 A1 10/2005 Furumi
2005/0228227 A1 10/2005 Weber
2005/0228697 A1 10/2005 Funahashi
2005/0231591 A1 10/2005 Abe
2005/0234507 A1 10/2005 Geske et al.
2005/0243169 A1 11/2005 Ono et al.
2005/0247081 A1 11/2005 Sakata et al.
2005/0250983 A1 11/2005 Tremaglio et al.
2005/0251112 A1 11/2005 Danitz et al.
2005/0251998 A1 11/2005 Bar-Or et al.
2005/0253044 A1 11/2005 Kuriyama
2005/0256370 A1 11/2005 Fujita
2005/0256373 A1 11/2005 Bar-Or et al.
2005/0256377 A1 11/2005 Deppmeier et al.
2005/0256424 A1 11/2005 Zimmon
2005/0264687 A1 12/2005 Murayama
2005/0267417 A1 12/2005 Secrest et al.
2005/0271340 A1 12/2005 Weisburg et al.
2005/0272978 A1 12/2005 Brunnen et al.
2005/0273085 A1 12/2005 Hinmane et al.
2005/0288545 A1 12/2005 Matsumoto et al.
2005/0288553 A1 12/2005 Sugimoto
2006/0015008 A1 1/2006 Kennedy
2007/0009060 A1 1/2007 Lavelle et al.

FOREIGN PATENT DOCUMENTS

EP 0 437 229 A1 7/1991
EP 0 689 851 A1 1/1996
EP 0 728 487 B1 11/2002
EP 1 300 883 A2 4/2003
JP 58-78635 A 5/1983
JP 05-31071 A 2/1993
JP 05-091972 A 4/1993
JP 06-105800 A 4/1994
JP 3372273 B2 4/1994
JP 06-254048 A 9/1994
JP 3219521 B2 9/1994
JP 07-8441 A 1/1995
JP 3482238 B2 12/1995
JP 10-113330 A 5/1998
JP 10-286221 A 10/1998

| | | | |
|---|---|---|---|
| JP | 11-216113 | A | 8/1999 |
| JP | 201-128933 | A | 5/2001 |
| JP | 2002-007134 | A | 1/2002 |
| JP | 2002-078675 | A2 | 3/2002 |
| JP | 2002-102152 | A | 4/2002 |
| JP | 2002-177197 | A | 6/2002 |
| JP | 2002-185873 | A | 6/2002 |
| JP | 2002-253481 | A | 9/2002 |
| JP | 2003-75113 | A | 3/2003 |
| WO | WO 93/13704 | A1 | 7/1993 |
| WO | WO 02/056756 | A2 | 7/2002 |
| WO | WO 2004/016310 | A2 | 2/2004 |
| WO | WO 2004/068840 | A2 | 8/2004 |
| WO | WO 2005/023082 | A2 | 3/2005 |

* cited by examiner

ADAPTER FOR USE WITH DIGITAL IMAGING MEDICAL DEVICE

CROSS-REFERENCE TO RELATED APPLICATION

The present application claims the benefit of U.S. Provisional Application No. 60/614,879, filed Sep. 30, 2004.

FIELD OF THE INVENTION

This invention relates to medical imaging devices in general and an imaging adapter and method for converting digital video signals to a standardized analog video format in particular.

BACKGROUND OF THE INVENTION

It has become well established that there are major public health benefits from regular endoscopic examinations of a patient's internal structures, such as the alimentary canals and airways, e.g., the colon, esophagus, stomach, lungs, uterus, urethra, kidneys, and other internal organ systems. Conventional imaging endoscopes used for such procedures generally comprise a flexible tube with a fiber optic light guide that directs illuminating light from an external light source to the distal tip where it exits the endoscope and illuminates a region to be examined. An objective lens and fiber optic imaging light guide communicating with a camera at the proximal end of the scope, or an imaging camera chip at the distal tip, produce an image that is displayed to the examiner. In addition, most endoscopes include one or more working channels through which medical devices, such as biopsy forceps, snares, fulguration probes, and other tools may be passed.

Conventional endoscopes are expensive hand-assembled medical devices costing in the range of $25,000 for an endoscope, and much more with the associated operator console. Because of the expense, these endoscopes are built to withstand repeated disinfections and use upon many patients. Conventional endoscopes are generally built of strong composite materials, which decrease the flexibility of the endoscope and thus can compromise patient comfort. Furthermore, conventional endoscopes are complex and fragile instruments that frequently need expensive repair as a result of damage during use or during a disinfection procedure.

Low cost, disposable medical devices designated for a single use have become popular for instruments that are difficult to sterilize or clean properly. Single-use, disposable devices are packaged in sterile wrappers to avoid the risk of pathogenic cross-contamination of diseases such as HIV, hepatitis, and other pathogens. Hospitals generally welcome the convenience of single-use disposable products because they no longer have to be concerned with product age, overuse, breakage, malfunction, and sterilization. One medical device that has not previously been inexpensive enough to be considered truly disposable is the endoscope, including, for example, a colonoscope, ureteroscope, gastroscope, bronchoscope, duodenoscope, etc. Such a low cost endoscope is described in U.S. patent application Ser. No. 10/406,149, filed Apr. 1, 2003, and in a U.S. Continuation-in-Part application Ser. No. 10/811,781, filed Mar. 29, 2004, and in a U.S. Continuation-in-Part patent application Ser. No. 10/956,007, filed Sep. 30, 2004, that are assigned to Scimed Life Systems, Inc., now Boston Scientific Scimed, Inc and are herein incorporated by reference.

The endoscope disclosed in U.S. patent application Ser. No. 10/406,149, U.S. patent application Ser. No. 10/811,781 and in U.S. patent application Ser. No. 10/956,007 contains a CMOS image sensor capable of producing digital image signals. Depending on the version of the sensor, the digitized image data may be transmitted from the distal tip of the endoscope in a serial or parallel format. The use of a digital video format enhances image quality by eliminating the introduction of noise during the transmission of the signal along the length of the endoscope. The analog-to-digital conversion is integral to the image sensor itself, further mitigating the opportunity for noise to be introduced into the image. Although the use of a digital image sensor produces better quality signals, there are some instances where it is desirable to use such a device with an existing analog video console. Therefore, there is a need for an imaging adapter and method for signal conversion that allows a medical imaging device having digital video output to be used with a system having conventional analog video input. Such an imaging adapter and method would allow a broader mass market to benefit from the advantages of using digital imaging in a low cost disposable endoscope.

SUMMARY OF THE INVENTION

To address these and other problems in the prior art, in one embodiment the present invention is a medical imaging system including a medical imaging device having an image sensor capable of producing an image signal in a digital video format. The medical imaging devices used with the system of the present invention may be reusable or single-use devices that are sufficiently inexpensive to manufacture such that the medical device can be considered as a single-use, disposable item. Also included in the system is an adapter that receives digital video image signals from the medical imaging device and provides a corresponding analog video signal to an analog processor.

In another embodiment, the present invention is an imaging adapter for use with an imaging medical device system. The imaging adapter receives digital image signals from a medical imaging device having a digital video output and converts the digital video signals to analog video in a standardized format for supply to an analog video console. In some embodiments, the imaging adapter includes a master clock in communication with a clock receiver in the medical imaging device. In further embodiments, the imaging adapter has means to provide power to one or more LEDs contained in the medical imaging device.

In another aspect, the present invention is a method of converting a serial digital video signal into a standardized analog video format. The method involves receiving an input serial digital video signal from a device having a remote image sensor, deserializing the digital video signal, and generating synthetic horizontal and vertical synchronization signals. The method includes interlacing the digital signal into standard line memories and converting the digital signal to an analog signal for output to an analog processor.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

In traditional endoscopic imaging systems, an endoscope intended for repeated clinical examinations detachably connects to a set of peripheral units typically including a light source unit, an analog video processor, a fluid source unit, and an air/vacuum unit. Once used, the endoscope is cleaned and disinfected (hereinafter referred to as a "reusable-type endoscope"). As discussed above, with the emergence of disposable medical imaging devices, the use of devices packaged in sterile wrappers decreases the risk of cross-contamination of diseases such as HIV, hepatitis, and other pathogens. In addition, single-use, disposable imaging endoscopes, such as the one described in U.S. patent application Ser. Nos. 10/406,149, 10/811,781 and 10/956,007 mentioned above, contain solid state imaging sensors capable of transmitting image data signals in a digital video format. Accordingly, in the absence of some form of adapter, in order to use a reusable or single-use endoscope with digital video output, it would be required to correspondingly replace a conventional analog video processor with a new digital video processor in order to accommodate the digital video output.

The present invention provides a system that enables an operator to use an endoscope having a digital video output with either a digital processor, or with conventional analog video processing equipment and peripherals, thus allowing a broader market to benefit from the advantages of enhanced image capability and reduced risk of cross-contamination inherent in single-use type endoscopes. By eliminating the requirement to purchase a separate digital video processor for use with a single-use endoscope, the present invention reduces the set up cost and space required in an examination room for using single-use endoscope devices. A further advantage of the present invention is that an imaging adapter allows an analog video processor and peripheral equipment to be interchangeable between a single-use type endoscope and reusable-type endoscope (e.g., specialized endoscopes), thereby allowing the examiner to select the most appropriate type of endoscope for a particular clinical procedure. The system can be used with a analog signal processor, by providing an adapter with digital-to-analog conversion in a remotely located camera board to enhance image quality by reducing the level of noise generated along the length of the endoscope.

Although the invention is described in reference to a low cost, single-use imaging endoscope, those skilled in the art will recognize that the invention is applicable to any other medical imaging devices that are single-use or reusable such as catheters, imaging guidewires, and the like, that include an image sensor that produces digital image signals.

Figure 1A:
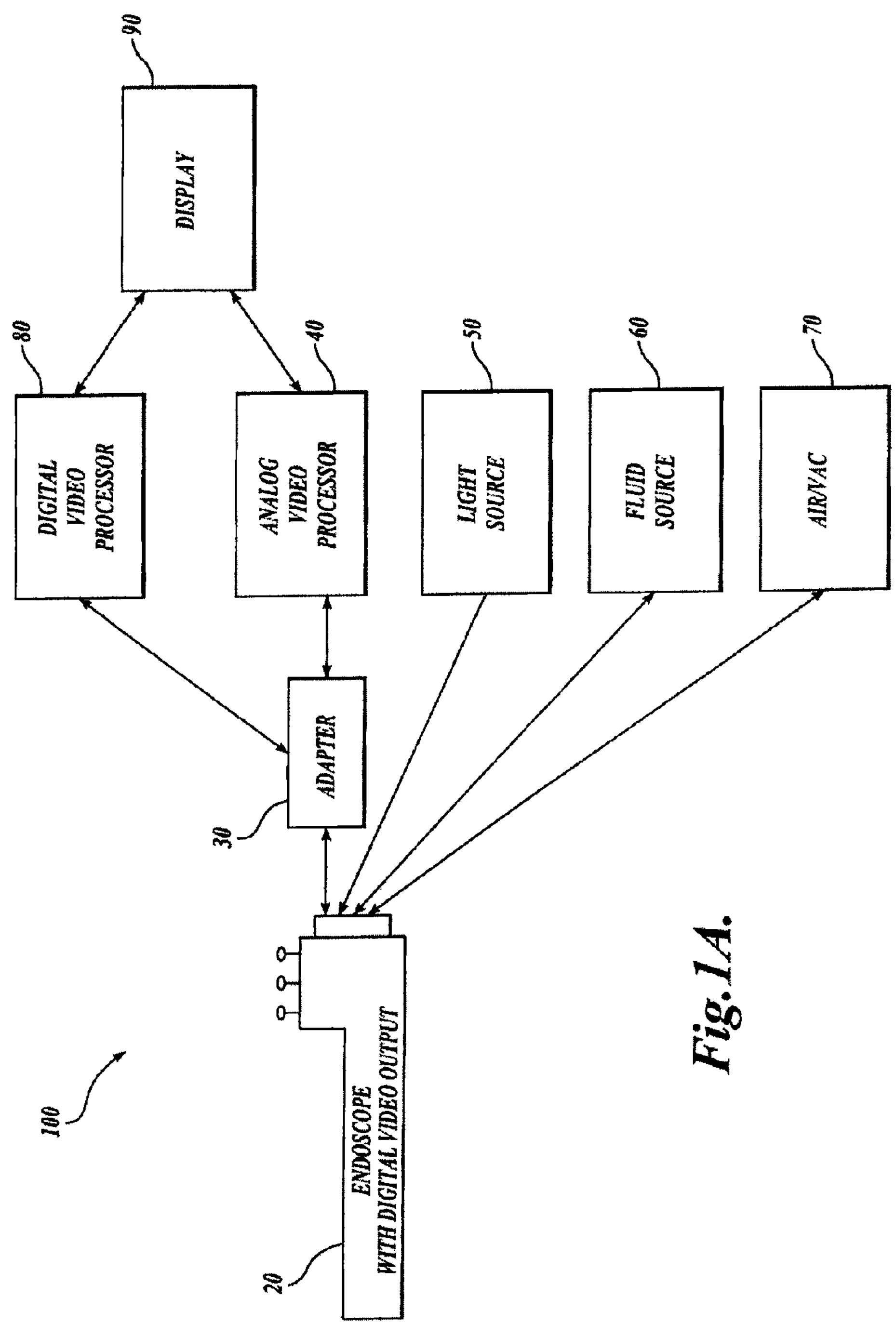
FIG. 1A is a block diagram of a medical imaging system comprising an imaging endoscope, an imaging adapter, and a conventional analog video console in accordance with an embodiment of the present invention.

FIG. 1A illustrates a representative embodiment of a medical imaging system 100 of the present invention that includes an endoscope 20 capable of transmitting video signals in a digital format (e.g., in serial or parallel format) connected to a conventional analog video processor 40 via an imaging adapter 30. The imaging adapter 30 converts the digital video output from the endoscope 20 into a standardized analog video format for use with an analog video processor 40, as discussed in more detail below. In the embodiment of the medical imaging system 100 shown in FIG. 1A, the adapter 30 is also shown as optionally connected to a digital video processor 80. The digital video processor 80 and the analog video processor 40 are each connected to an image monitor/display 90 that displays the video image captured by the endoscope 20. In an alternative embodiment, the digital video processor 80 is connected directly to the endoscope 20 and the analog video processor 40 is connected to the endoscope 20 via the imaging adapter 30. In one embodiment, the adaptor 30 is housed within the analog video processor. In another embodiment, the adaptor 30 is external to the analog video processor.

As further shown in FIG. 1A, the single-use type endoscope 20 is additionally connected directly to a set of peripheral support devices including a light source 50, a fluid source 60, and an insufflation air/vacuum source 70. While the embodiment of the imaging adapter 30 in FIG. 1A is shown to be only connected to the imaging processors 40 and 80, in alternative embodiments, the imaging adapter 30 may have additional connectors capable of functionally connecting the single-use type endoscope 20 to other peripheral support devices, such as the light source 50, the fluid source 60, and the insufflation air/vacuum source 70.

Figure 1B:
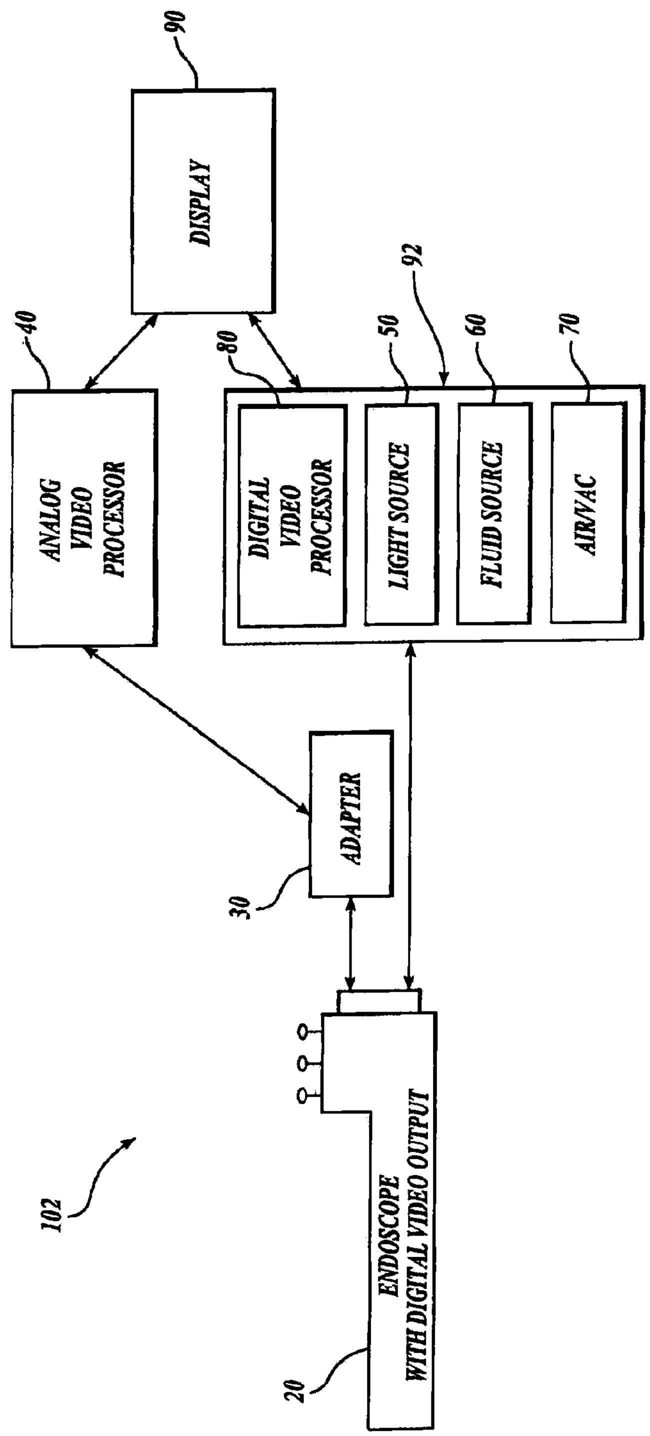
FIG. 1B is a block diagram of an alternative embodiment of a medical imaging system comprising an imaging endoscope, an imaging adapter connected to a conventional analog video console, and a control unit including a digital video processor in accordance with an embodiment of the present invention.

In an alternative embodiment of the medical imaging system 102, shown in FIG. 1B, the analog video processor 40 is connected to the adapter 30, which is in turn removably attached to the endoscope 20. The system 102 also includes the digital video processor 80 and one or more of the peripheral support devices (e.g., the light source 50, the fluid source 60, and the air/vacuum source 70) which may be contained in a single console 92 that is also removably attached to the proximal end of the endoscope 20. The console 92 may be mounted on a wheeled unit so that it can be placed near a patient during an examination procedure.

Figure 2:
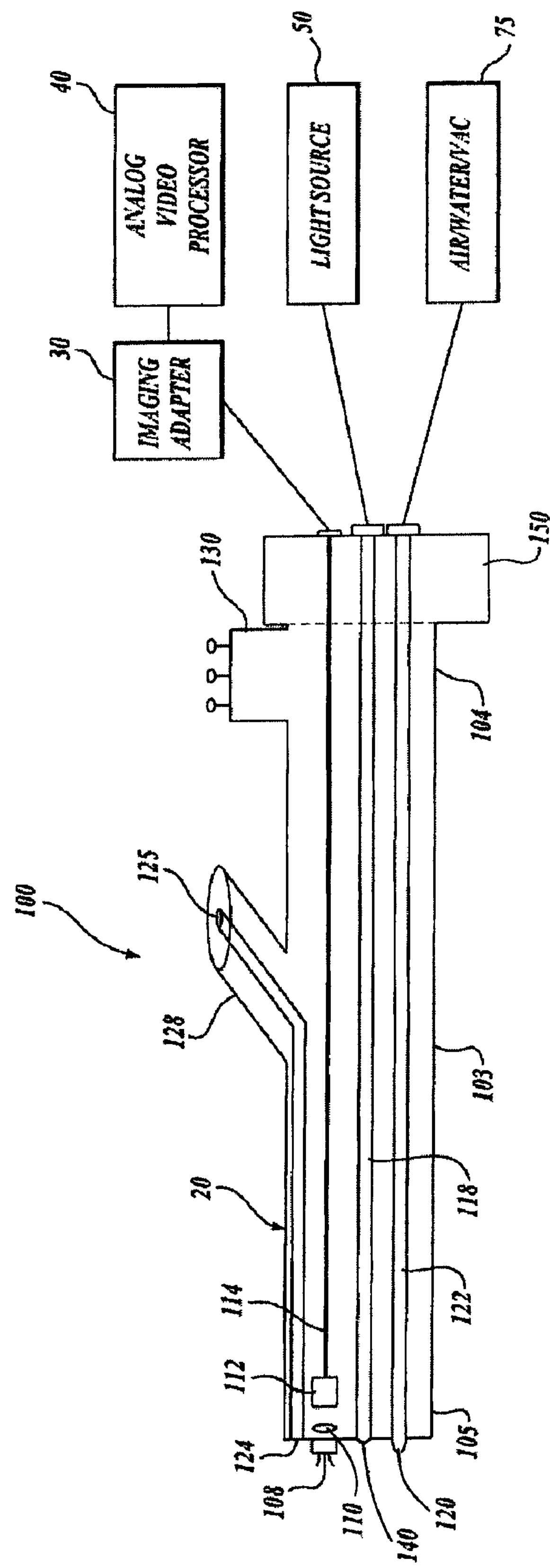
FIG. 2 is a cross-sectional view of a representative embodiment of an endoscope attached to an imaging adapter and other peripheral support devices in accordance with an embodiment of the present invention.

FIG. 2 shows a cross-sectional view of a representative embodiment of a single-use type endoscope 20 included in the medical imaging system 100. As shown in FIG. 2, the representative single-use type endoscope 20 comprises a flexible elongated shaft 103 having a distal tip 105 that is advanced into a patient's body and a proximal end 104 attached to a proximal connector 150. The proximal connector 150 has several lumens and connections that connect to various peripheral devices including a light source 50 and an air/water/vacuum source 75. In the embodiment shown in FIG. 2, the lumens and electrical connections are positioned adjacent to one another on the same side of the proximal connector 150. In an alternative embodiment, the lumens and electrical connections may be positioned on different sides of the proximal connector 150 (not shown).

A controller portion 130 is located at the proximal end 104 of the endoscope that includes valves, actuators, switches or the like that control the delivery of fluid, light, air/gas, and/or images to and from the distal tip of the endoscope. The controller portion 130 may be integrally formed with the endoscope (as shown in FIG. 2), or in an alternative embodiment, the controller portion 130 may be separately formed and attached to the endoscope 20.

In the embodiment shown in FIG. 2, the single-use endoscope 20 also includes an entrance to a working channel lumen 125 into which a physician can insert a medical device, such as biopsy forceps, a snare, and the like, for surgical manipulation in a patient's body.

With continued reference to FIG. 2, the distal tip 105 of the single-use type endoscope 20 also includes an irrigation port 120 connected to a fluid line 122 that connects to a fluid source 75. Also included on the distal tip 105 is an access port 124 that defines the distal opening of a working channel 125. In the embodiment shown in FIG. 2, an external light source 50, such as an incandescent light source, such as a halogen lamp or solid state light source such as an assembly of one or more LEDs, supplies illumination light by way of a fiber bundle that passes from the light source 50 through a cable into the proximal connector 150 and into the endoscope body 103 through a light guide 118 and emerges at the distal tip 105 of the single-use type endoscope 100 at an illumination lens port 140. In an alternative embodiment of the system 100 (as shown, for example, in FIG. 4), illumination is provided by one or more light emitting diodes (LEDs) positioned at or near the distal tip 105 connected to one or more corresponding illumination ports. The LEDs may be high intensity white light sources or may comprise monochromatic light sources such as infrared (IR), red, green, blue or ultra-violet (UV) LEDs.

With substantially monochromatic LEDs, images in different spectral bands may be obtained due to illumination with any one or more individual wavelengths. White light images may be obtained by the simultaneous or sequential illumination of tissue of the monochromatic LEDs and combining individual images obtained at each illumination wavelength. If sequential illumination with monochromatic LEDs is employed, as an alternative, a monochrome image sensor can be used. Electrical power may be supplied to the LEDs via an adapter connected to one of the peripheral devices in the system, such as the analog or digital processor, as described in more detail below.

Referring again to FIG. 2, the distal tip 105 also includes an imaging assembly 108 that includes an objective lens assembly 110 and an image sensor 112, such as a CMOS solid state image sensor that captures reflected light to produce image signals representative of the illuminated scene. A circuit board or flex circuit (not shown) containing circuitry to transmit signals to a video processor is secured behind the image sensor 112. Image signals produced by the image sensor 112 are transmitted via a signal line 114 to a display device (not shown), to be viewed by an examiner. The image sensor 112 is preferably a low light sensitive, low noise, CMOS color imager with VGA resolution or higher, such as SVGA, SXGA, XGA or UXGA. If less resolution is required, a ½ or ¼ VGA sensor could also be used. Image sharpness should be consistent with FDA Guidance Documents for Endoscopes that suggests resolution of 5 line pairs per millimeter on an object surface, concentric with the entrance pupil, at an object distance of approximately 10 mm. This is consistent with the use of a VGA (640×480) pixel color imager, such as those manufactured using CMOS or CCD technology by companies such as Micron, Inc. or ST Microelectronics. For conventional video systems, a minimum frame rate of 25 to 30 fps is required to achieve the appearance of real-time video. An important advantage of the use of the digital image sensor 112 is that the analog-to-digital conversion occurs on the imager rather than on a separate chip at the distal tip or in the drive electronics at the proximal end of the endoscope, thereby providing a high quality image with an more accurate representation of the image sensor output.

In operation of the medical imaging system 100, an operator prepares the single-use endoscope 20 for clinical use by attaching the proximal connector 150 to a first connector on the imaging adapter 30. The imaging adapter 30 is in turn connected to the analog video processor 40 via a second connector. The endoscope 20 may also be additionally attached to other peripheral support devices, such as the light source 50 and the fluid/air/vacuum source 75 as required by the clinical procedure. During clinical use, the distal tip 105 of the endoscope 20 is inserted into a patient, and the imaging system 108 captures a reflected illumination light from an examination area. The light is directed onto the image sensor 112, and a digital video image signal is sent along image signal line 114, through the proximal connector 150 and into the imaging adapter 30. In the imaging adapter 30, the digital video signal is converted into a conventional analog video signal and sent to the analog video processor 40, as described in more detail below. After clinical use, the proximal connector 150 on the single-use endoscope 20 is disconnected from the imaging adapter 30 and from any other attached peripheral devices, and the single-use endoscope 20 is then discarded as medical waste to prevent improper reuse.

Figure 3:
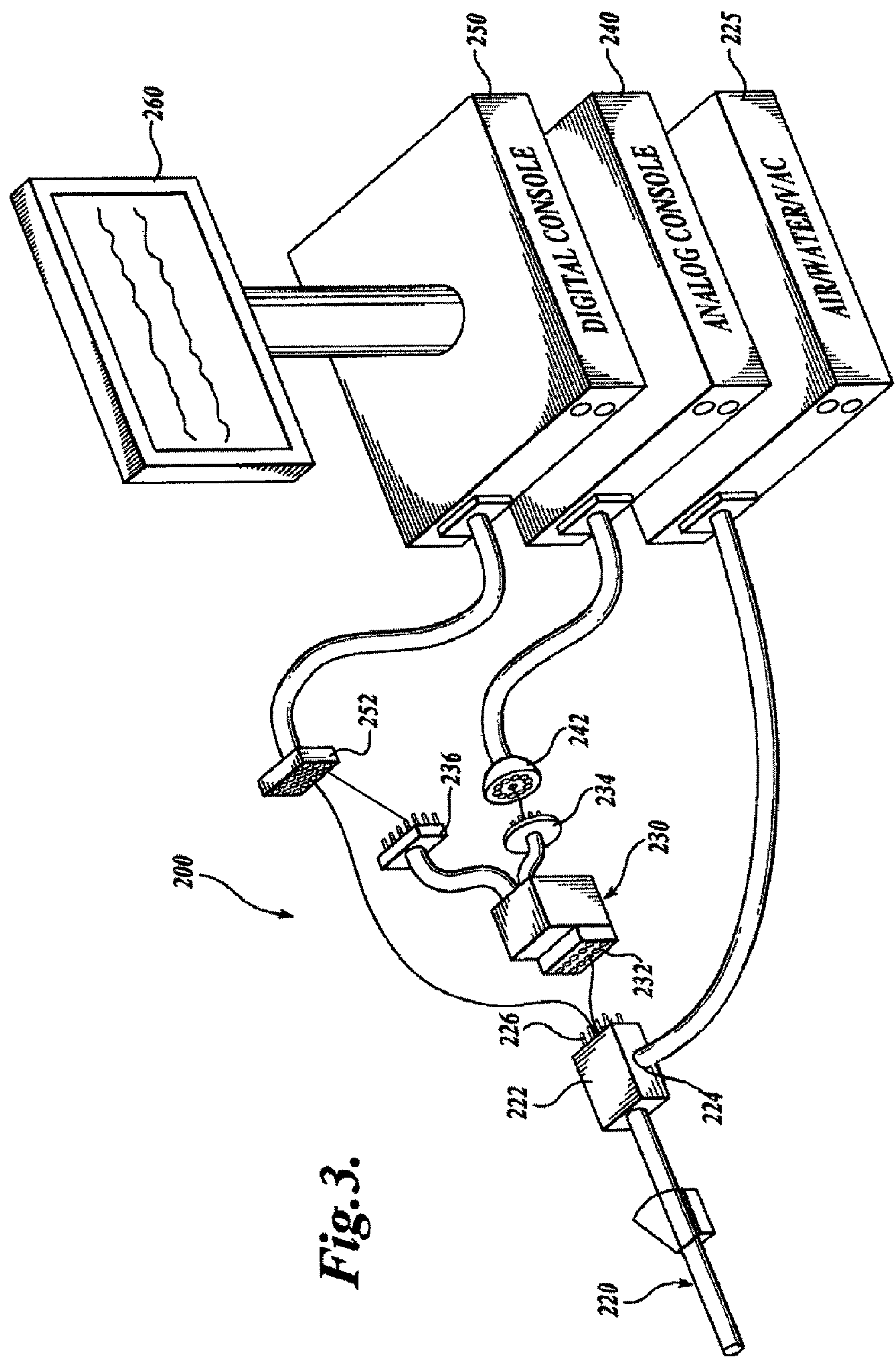
FIG. 3 is a perspective view showing a representative set of corresponding connectors on an endoscope, imaging adapter, and analog and/or digital video consoles in accordance with an embodiment of the system of the present invention.

FIG. 3 illustrates a system 200 having a representative set of interconnecting structures capable of connecting a single-use endoscope 220, an imaging adapter 230, and an analog video processor 240 in accordance with another embodiment of the present invention. As shown in FIG. 3, the single-use endoscope 220 has a proximal connector 222 with a first outlet 224 containing one or more lumens that connect to a support unit 225 that supplies air/water/vacuum and a second electrical connector outlet 226 that forms an electrical connection with a first connector 232 on the imaging adapter 230. The imaging adapter 230 shown in FIG. 3 also includes a second connector 234 for connecting to a receptacle 242 that is part of an analog processor 240. An optional third connector 236 that is part of the adapter 230 connects to a receptacle 252 that is part of the digital video processor 250.

While the primary purpose of the adapter 230 is to provide a connection from the endoscope 220 to the analog console 240, as shown in FIG. 3, the optional connection 236 that connects to the digital processor 250, such as a PC, may be provided in order to allow digital data to be recorded and stored on any digital medium associated with the digital processor 250. Images produced by the digital processor 250 may also be printed on a digital printer, sent to a network server (not shown), or saved to a computer readable medium such as a floppy disc, CD, DVD, and the like for later retrieval and analysis by medical personnel. A monitor 260 is shown attached to the digital video processor 250 and may be provided with analog video signals from the analog processor 240 and/or digital video signals from the digital processor 250 using methods well known by those of skill in the art.

It will be understood by those of skill in the art that the connectors shown in FIG. 3 are not limited to a particular type of connector (e.g., pin type) or specific configuration of contacts, but the imaging adapter 230 may be modified to have a first connector adapted to connect to a proximal connector of any type of endoscope system that produces digital video signals and a second connector adapted to connect to a video processor capable of receiving an analog signal in a conventional format. For example, the connectors on the adapter 230 may be any type of suitable connector such as, for example, an end plug, pin or edge connector. In an alternative embodiment, the adapter 230 is non-removably attached to the imaging device. In another embodiment, the adapter is integrally formed with the imaging device. In some embodiments, at least one connector on the imaging adapter 230 also provides power to the endoscope 220 as described in more detail below.

In one embodiment of the invention, the imaging adapter 230 additionally includes an image processing subsystem having components capable of decoding and converting the input digital video signals received from the image sensor at the distal tip of the endoscope into analog video signals in a standardized format according to any suitable method such as, for example, the image processing method described herein below.

Figure 4:
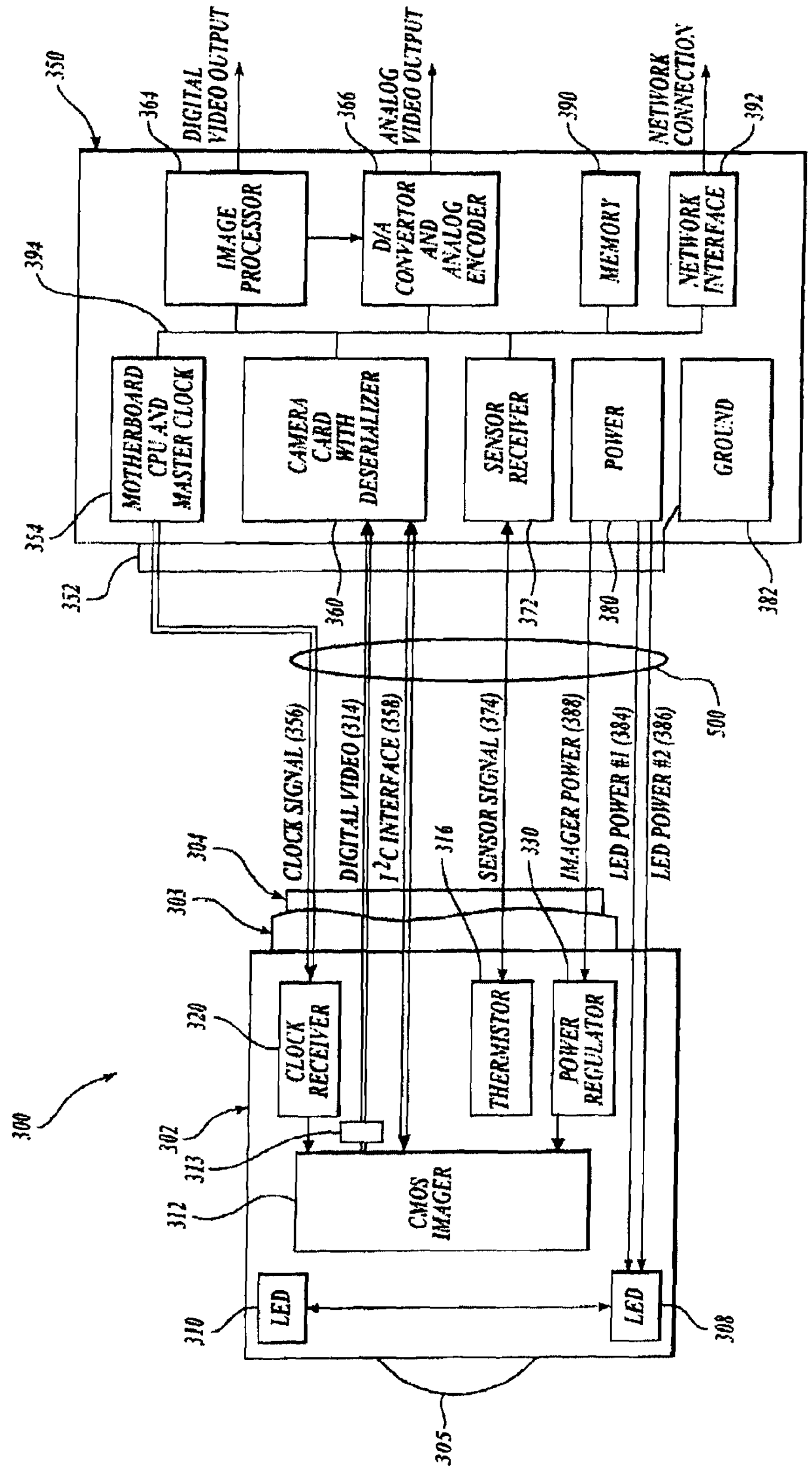
FIG. 4 is a block diagram showing the components and signals sent between a representative imaging adapter and a distal tip of a representative imaging endoscope in accordance with an embodiment of the present invention.

FIG. 4 illustrates the major components of a representative embodiment of a medical imaging system 300. The system 300 includes an endoscope 303 with an image sensor 312 located in a distal tip 302 that is in communication with an imaging adapter 350 that has image processing system. As shown in FIG. 4, the endoscope 303 has a lens 305 and an imaging sensor 312 at its distal tip 302 capable of producing digital image signals. The distal tip 302 also includes a clock receiver 320, a thermistor 316, a power regulator 330 connected to the image sensor 312, and a pair of LEDs 308, 310 that supply an illumination light for the image sensor 312. A proximal connector 304 connects the endoscope 303 to a corresponding connector 352 on an imaging adapter 350.

The imaging adapter 350 includes a camera card 360, a motherboard and master clock 354, a temperature sensor receiver 372, an image processor 364, a digital-to-analog converter 366, a memory 390, and a network interface 392, all connected via a bus 394. The camera card 360 contains conventional circuitry for deserialization, synchronization, color space conversion, automatic gain control, white balance initialization, and a pixel correction interlacer. The camera card 360 further includes its own EPROM for storing firmware that may be updated, if necessary, and a frame memory for storing video frames. The camera card 360 also generates control signals that are sent to the imager 312 in the distal tip 350 of the imaging device. The image processor 364 performs video processing functions and supplies digital video output to a video display monitor and/or other remote digital display.

Once processed by the image processor 364, the digital video signal is output in any desired display format such as, for example, via Firewire, USB, parallel, serial or in a compressed formats, and the like. The digital video data may be compressed using standard compression techniques such as MPEG-1, MPEG-2, and MPEG-4.

The image processor 364 is also connected to the digital-to-analog converter 366, which converts digital video to analog format and encodes analog video in standard format for output to an analog video console or other remote analog display or capture devices (not shown). The analog signal is output in a conventional format such as NTSC or PAL, suitable for output as composite video, S-video, and/or RGB analog video to enable the use of a conventional analog console.

Also included in the imaging adapter 350 is the network interface card 392 connected to the motherboard 354 via the bus 394. The network interface card 392 forms an optional connection with a remote display device, a graphics processor, a control unit or other remote device, and may transmit image signal data and other operating parameters. Those of ordinary skill in the art will appreciate that the network interface card 392 includes the necessary circuitry for connecting the imaging adapter 350 directly to a LAN or WAN, or for connecting remotely to a LAN or WAN with various communication protocols, such as the TCP/IP protocol, the Internet Inter-ORB protocol, any of the various wireless protocols (e.g., the IEEE 802.1x family), and the like. As further shown in FIG. 4, the motherboard 354 is connected to the memory 390 via the bus 394. The motherboard 354 may also interface with an I/O device interface that is connected to peripheral devices (not shown) such as, for example, a handheld controller, keyboard, touch screen, printer, storage devices, servers, a hospital information network, and other peripheral devices.

In one embodiment, the imaging adapter 350 is an integrated computing platform, including the motherboard 354 that provides the standard PC type connectors, including serial ports, parallel ports, one or more PCI slots, an Ethernet port, USB ports, microphone in, sound out, etc.

With continued reference to FIG. 4, a plurality of signal lines are sent between the proximal connector 304 and the imaging adapter 350 along a cable 500, including one or more power signal lines to the LEDs 384, 386, a power signal line to the imager 388, a clock signal line 356, a digital video signal line 314, a temperature sensor signal line 374, and an imager control signal line 358. The clock signal line 356 transmits signals from the remote master clock 354, located in the imaging adapter 350, to the clock receiver 320 in the distal tip 302. The digital video signal line 314 transmits digital video data from the imager 312 to the camera card 360 located in the imaging adapter 350. The imager control signal line 358 (e.g., an $I^2C$ interface) transmits bidirectional control signals between the imager 312 and the camera card 360. The temperature sensor signal line 316 transmits temperature signals from the thermistor 316 to a thermistor receiver 372 in the imaging adapter 350 in order to monitor the operating temperature of the distal tip 302. The adaptor 350 may include a safety feature that shuts off power to the distal tip 302 if the thermistor signal indicates that the distal tip 302 is overheating. A power source 380 is included in the adapter 350, which is grounded via a ground lead 382. The power source 380 supplies isolated power along signal lines 384 and 386 to drive the LEDs 308 and 310 in the distal tip 302. The gain control of the system 300 may be implemented by adjusting the intensity of the illumination (current supplied to the LEDs) via the power lines 384, 386 and/or by adjusting the gains applied to the video signals sent via the signal line 314 from the CMOS image sensor 312. The power regulator 330 in the distal tip 302 also receives power from the power source 380 in the imaging adapter 350, via the signal line 388, and regulates the power provided to the image sensor 312.

The image sensor 312 produces digital video and synchronization signals that are transmitted along the signal line 314 that are sent to a camera card 360 in the adapter 350. The output of the image sensor 312 may be in either parallel digital format or serial digital format. If the image sensor provides parallel data output, the data stream may be serialized off the imager chip with a separate serializer chip 313 that is optionally located in the distal tip 302. If the digital video signal received on the signal line 314 is in a serial format, it is restored to a parallel format via a deserializing operation performed on the camera card 360, via a field programmable gate array device.

By incorporating a serializer into the image sensor 312, a highly compact distal tip 302 can be fabricated. The serial data format allows for a lower wire count in the cable, and hence a small diameter cable may be used in the endoscope 303. The reduced cable size allows the diameter of the endoscope 303 to be minimized. Also, the cost of an imager 312 with an integrated serializer is less than the cost of a separate imager and serializer and their interconnects. A further advantage of using a serial data stream is that the data rate of the signal line 314 is considerably higher than that of each parallel data line. For example, a 10-bit imager will typically produce a serial data rate that is 12 times faster than its parallel data rate. Accordingly, in one embodiment of the system 300, the image sensor 312 comprises a VGA CMOS image sensor with 640×480 active pixels and an on-chip serializer that transmits image data to the adapter 350 in a serial format via the signal line 314. Such a CMOS image sensor is available as Model No. MI-370 from Micron Electronics of Boise, Id.

As shown in FIG. 4, a clock receiver 320 located at the distal tip 302 of the endoscope receives a clocking signal 356 produced by a remote clock source 354 located in the adapter 350. The clocking signal 356 may be, for example, a low voltage differential signal ("LVDS") clocking signal or other source that can be used as a reference to transmit data from the distal tip 302 through the endoscope 303 to the adapter 350. By locating the master clock 354 remotely in the adapter 350, a reduction in the size of the distal tip 302 is possible along with an associated reduction in cost of the endoscope such that it may be disposed of as medical waste after a single use.

In a preferred embodiment of the system 300, the imaging adapter 350 receives digital signals transmitted from a low cost imaging endoscope as described in U.S. patent application Ser. No. 10/406,149, filed Apr. 1, 2003, and in a U.S. Continuation-in-Part Application Ser. No. 10/811,781, filed Mar. 29, 2004, and in a U.S. Continuation-in-Part patent application Ser. No. 10/956,007, filed Sep. 30, 2004, that are assigned to Scimed Life Systems, Inc., now Boston Scientific Scimed, Inc and are herein incorporated by reference. The endoscope disclosed in U.S. patent application Ser. No. 10/406,149, U.S. patent application Ser. No. 10/811,781 and U.S. patent application Ser. No. 10/956,007 contains a CMOS image sensor capable of producing digital image signals that are transmitted in a serial format, a pair of LEDs in the distal tip, and lumens for air/gas and fluid that are connected to a manifold in a proximal connector of a control unit. In accordance with this embodiment, the imaging adapter has connectors capable of functionally connecting the lumens in the endoscope to corresponding air/gas/fluid tubing in the manifold of the proximal connector.

Figure 5:
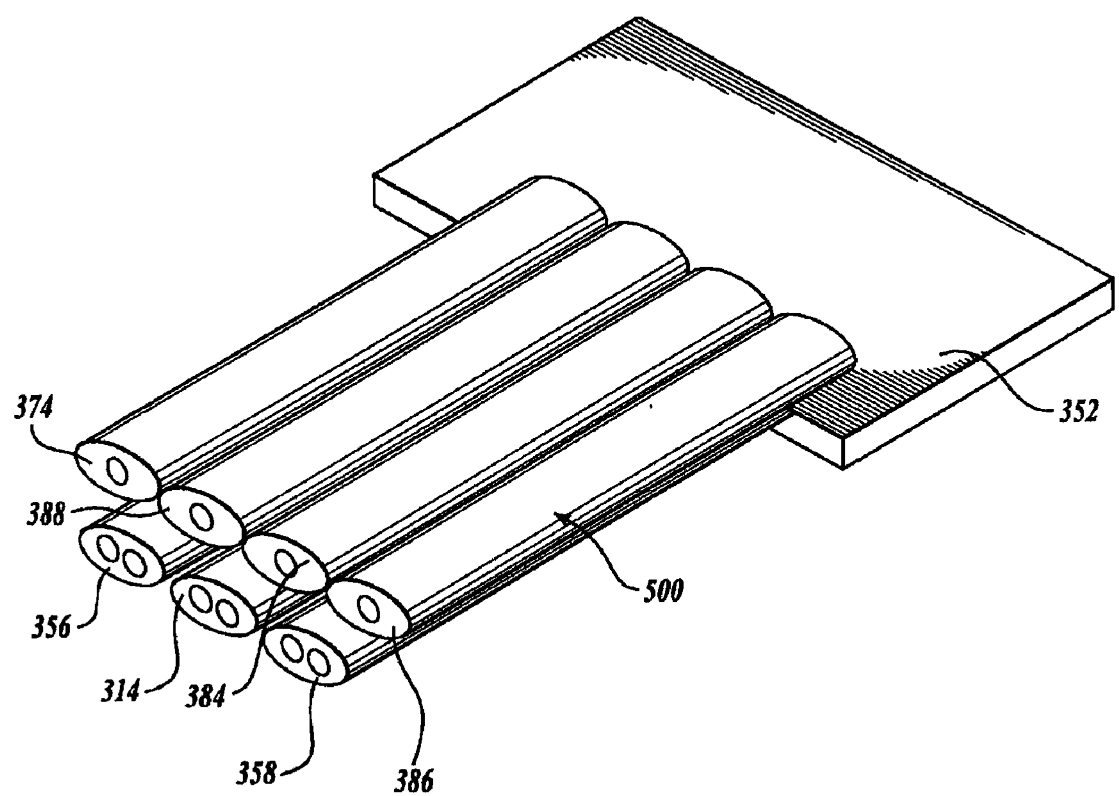
FIG. 5 is a cross-sectional view of a representative cable for connecting the proximal end of an imaging endoscope to an imaging adapter or control unit in accordance with an embodiment of the invention.

FIG. 5 illustrates one embodiment of the cable 500 that carries a plurality of signals between the proximal end of the endoscope 303 and the imaging adapter 350. The cable 500 has a first end connected to the proximal connector 304 on the endoscope 303 and a second end connected to the connector 352 on the imaging adapter 350. The cable 500 may be connected to the connector 304 and 352 by any suitable means such as, for example, pogo pins, end plug, edge connector, and the like, or may be integrally formed with the connector 304 or 352. In the embodiment shown in FIG. 5, the cable 500 includes the following signals carried on a pair of wires: the clock signal 356, the digital video signal 314, and the bidirectional imager control signal 358. The wire pairs may be differentially driven, twin axial cables capable of transmitting low voltage differential signals. In one embodiment of the system 300, the image signals produced by the image sensor 312 are transmitted differentially, in serial digital format, along the signal line 314 in the cable 500 in order to minimize susceptibility to external interference or common node noise. For example, the signals transmitted along the signal line 314 may be sent at 162 Mbps LVDS signaling via a suitable micro-coaxial or micro-twinaxial cable. The cable 500 also includes the following signals carried on single wires: the temperature sensor signal 374, the imager power signal 388, and the LED power signals 384, 396.

In operation of the medical imaging system 300, the lens 305 and CMOS imager 312 capture reflected light to produce digital signals representative of the illuminated scene. The digital image signals are sent via the signal line 314 into the camera card 360. The image signals may be in serial or parallel format, and may include embedded synchronization signals. Once the image signals are received in the camera card 360, the serial digital signals are deserialized and decoded using the appropriate decoding process corresponding to the type of signal. The digital signals are then further processed by the camera card 260 and/or the image processor 364. Image processing may include, for example, color space conversion and demosaicizing to convert the signals into the red-green-blue (RGB) color video format, or alternatively, the video signals may be converted into the YCCr format. The digital signal may be output to a digital display monitor (e.g., an LCD, CRT, or plasma display) in any suitable format such as, for example, the DVI standard. In some embodiments of the system 300, the digital signal is converted from digital to analog in the digital-to-analog converter 366 and interlaced to transform it from a progressive scan format into a standard interlaced analog video format for output to an analog processor and display device.

In another aspect, the present invention is a method of converting serial digital video signals to a standardized analog video format. In accordance with this aspect of the invention, a serial digital video signal is sent from a solid state imaging sensor and associated electronics as described herein. The method provides digitized serial image data from, for example, an imager in a the distal tip of an endoscope, which is transmitted along the length of the shaft to a control unit or imaging adapter where the digital image is deserialized, processed, and converted from digital to analog format. The method provides several advantages, including the elimination of noise introduced during signal transmission, increased speed of image signal transmission, and a minimal wire count required for signal transmission, while allowing the use of a conventional analog console.

Figure 6:
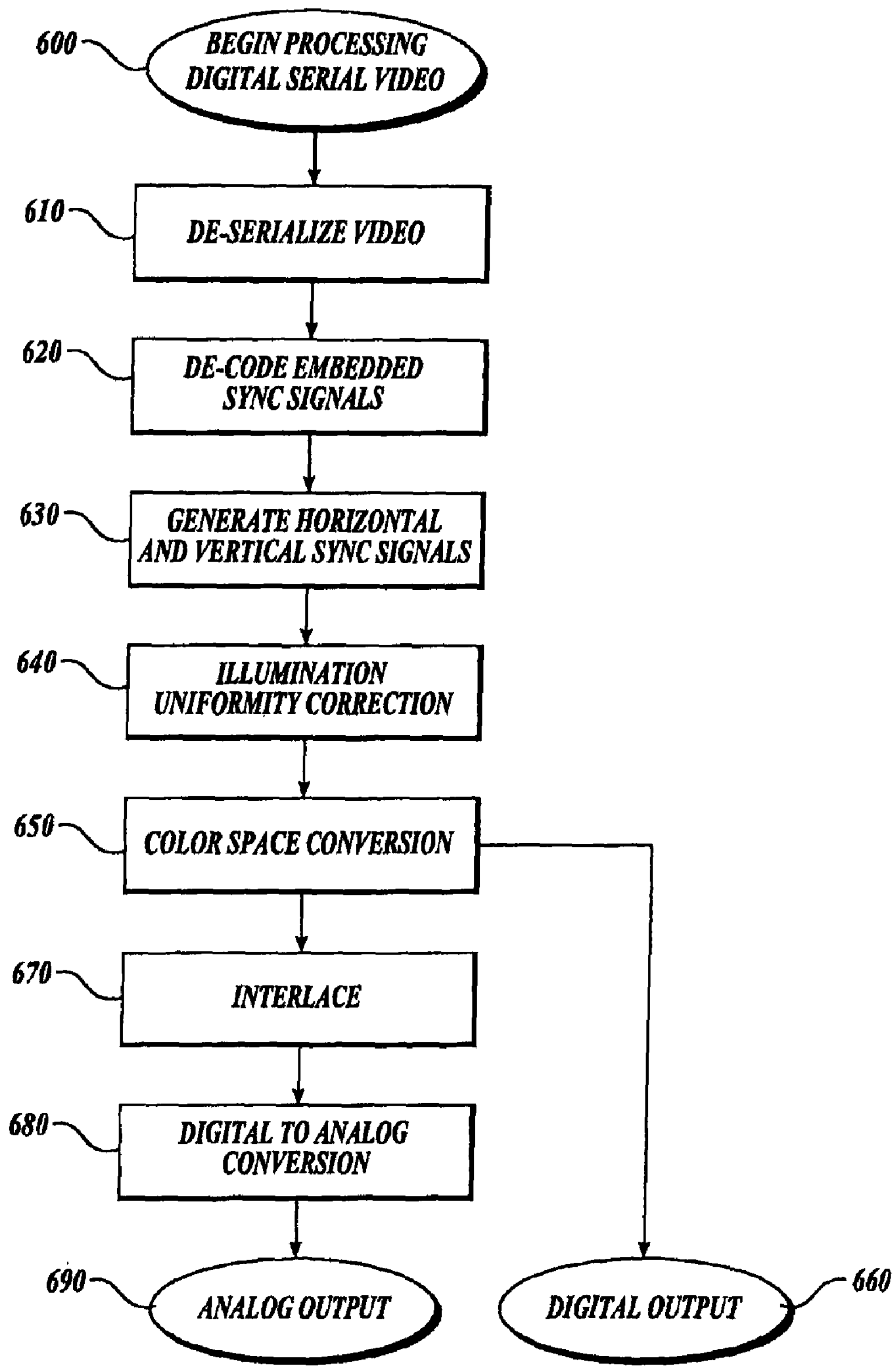
FIG. 6 is a flow diagram showing a method of converting digital serial video signals sent from an imaging sensor in a medical imaging device into an analog video standardized format in accordance with an embodiment of the present invention.

A representative embodiment of an image processing routine is shown in FIG. 6. The video image processing routine starts at 600 with serial digital video input data. At 610, the digital video data is deserialized by a deserializer. The deserialized digital video data is decoded at 620 using a decoding process that corresponds to the encoded input data. A video decoder may be designed to decode video data according to any one or a combination of standards. For example, the video may be decoded by decompressing a bitstream encoded to comply with MPEG standard format. In some embodiments, the serial digital video is in a progressive scan format that includes standard embedded synchronization signals that are also decoded.

At 630, standard, synthetic horizontal and vertical synchronization signals are generated (e.g., in EAV/SAV codes) and added to the digital video data.

At 640, an illumination uniformity correction is applied to the digital data to correct for illumination fall off that may have occurred during image capture and/or image signal transfer. The illumination correction may be applied as a function of the field of view, vignetting in the lens, or cosine fall-off that may be encountered in the imaging system. The dynamic range of the image can also be improved via a look-up table or functional calculation that remaps the signal luminance for each pixel.

At 650, the digital video data is color space converted and demosaicized to interpolate the color for each pixel into the red-green-blue ("RGB") color video format. The color signal for each pixel is calculated via a demosaicing process that is used with pixilated color CMOS sensors. Various color space conversions may be used to enhance the image signal and provide the data in a format consistent with additional enhancement methods, such as smoothing and sharpening. For example, a sharpening algorithm may be applied to the image data to improve the perceived sharpness and resolution of the image (e.g., a 3×3, 5×5, or 7×7 sharpening kernel).

At 660, the digital video is output to a digital image processor, digital display monitor, or other device.

At 670, the digital video data is interlaced to transform it from a progressive scan format into standard line memories.

At 680, the digital video data in standard line memory format is converted from digital to standardized analog format via a digital-to-analog (D/A) converter and analog encoder.

The analog signal is output to an analog processor or analog display device at 690 in a standardized format, such as NTSC or PAL, suitable for output as composite video, S-video, and/or RGB analog video.

The method 600 can be performed in the imaging adapter 350, as described herein. Alternatively, the method 600 can be performed using a set of suitable components in an image processor in a control unit attached to an endoscope, or on an imaging board located inside an endoscope. The imaging board can enhance the images received or can provide video effects such as zoom, color changes, highlighting, etc., prior to display of the images on the video display.

While embodiments of the invention have been illustrated and described, it will be appreciated that various changes can be made therein without departing from the scope of the invention.

The embodiments of the invention in which an exclusive property or privilege is claimed are defined as follows:

1. A method of converting serial digital video signals to a standardized analog video format, the method comprising:
- receiving an input serial digital video signal from a device having a remote image sensor;
- deserializing the input digital video signal;
- decoding the deserialized input digital video signal;
- generating synthetic horizontal and vertical synchronization signals;
- interlacing the digital signal into standard line memories;
- converting the digital signal into a standardized analog video format; and
- applying an illumination uniformity correction to the digital video signal;
- wherein the illumination uniformity correction is applied as a function of at least one of a field of view, vignetting in a lens, and a cosine fall-off in an imaging system.

2. The method of claim 1, wherein the device having a remote image sensor is a single-use endoscope.

3. The method of claim 1, wherein the remote image sensor is a solid state imaging sensor.

4. The method of claim 1, wherein decoding the deserialized input digital video signal includes decoding embedded synchronization signals.

5. The method of claim 1, wherein the synthetic horizontal and vertical synchronization signals are added to the digital video signal.

6. The method of claim 1, further comprising:
- applying a color space conversion to the digital video signal.

7. A method of converting serial digital video signals to a standardized analog video format, the method comprising:
- receiving an input serial digital video signal from a single-use endoscope having a remote image sensor;
- deserializing the input digital video signal;
- decoding the deserialized input digital video signal;
- generating synthetic horizontal and vertical synchronization signals;
- interlacing the digital signal into standard line memories; and
- converting the digital signal into a standardized analog video format;
- wherein the single-use endoscope is configured to cooperate with an adapter, and wherein the step of receiving an input serial digital video signal includes the adapter receiving the input serial digital video signal.

8. The method of claim 7, wherein converting the digital signal into a standardized analog video format creates an analog video signal, the method further comprising:
- sending the analog video signal from the adaptor to an analog video processor.

9. The method of claim 7, further comprising:
- transmitting a temperature signal from a thermistor in the single-use endoscope to a temperature sensor receiver in the adapter.

10. The method of claim 9, further comprising:
- terminating power to the single-use endoscope based on the temperature signal received by the temperature sensor receiver.

11. The method of claim 7, further comprising:
- transmitting a clocking signal from a remote clock source in the adapter to a clock receiver in the single-use endoscope.

12. The method of claim 7, further comprising:
- transmitting a power signal from a power source in the adapter to a power regulator in the single-use endoscope; and
- regulating power delivered to the remote image sensor in the single-use endoscope.

13. The method of claim 12, further comprising transmitting a power signal from the power source to an illumination source in the single-use endoscope.

14. The method of claim 7, further comprising:
- connecting the adapter to a peripheral support device such that the adapter provides communication between the single-use endoscope and the peripheral support device.

15. The method of claim 14, wherein the peripheral support device includes at least one of a vacuum source, a gas source, and a fluid source.

16. The method of claim 7, wherein the adapter includes a deserializer.

17. The method of claim 7, wherein a camera card in the adapter is configured to receive the input serial digital video signal.

18. The method of claim 17, wherein a control signal line transmits bidirectional control signals between the camera card and the remote image sensor.

* * * * *